United States Patent [19]

Schulz

[11] Patent Number: 5,377,669
[45] Date of Patent: Jan. 3, 1995

[54] SAPPHIRE PROTECTIVE COVERING FOR MEDICAL ENDOSCOPE

[75] Inventor: Dieter Schulz, Muehlheim, Germany

[73] Assignee: Henke-Sass, Wolf GmbH, Tuttlingen, Germany

[21] Appl. No.: 45,356

[22] Filed: Apr. 2, 1993

[30] Foreign Application Priority Data

Apr. 6, 1992 [DE] Germany .................. 4211547

[51] Int. Cl.$^6$ ................................ A61B 1/06
[52] U.S. Cl. ........................... 128/6; 385/117
[58] Field of Search ............... 128/6, 4, 7, 8; 385/117

[56] References Cited

U.S. PATENT DOCUMENTS

| | | | |
|---|---|---|---|
| 4,219,013 | 8/1980 | Okada | 128/6 X |
| 4,772,093 | 9/1988 | Abele et al. | 385/117 X |
| 4,790,295 | 12/1988 | Tashiro | 128/6 |
| 4,802,460 | 2/1989 | Ohkuwa et al. | 128/6 |
| 4,807,594 | 2/1989 | Chatenever | 128/4 |
| 4,807,597 | 2/1989 | Tsuno et al. | 128/6 |
| 4,850,342 | 7/1989 | Hashiguchi et al. | 128/6 |
| 4,878,485 | 11/1989 | Adair | 128/6 |
| 4,947,245 | 8/1990 | Ogawa et al. | 128/6 X |
| 5,051,824 | 9/1991 | Nishigaki | 128/6 X |

Primary Examiner—Richard J. Apley
Assistant Examiner—Donna L. Maraglio
Attorney, Agent, or Firm—McAulay Fisher Nissen Goldberg & Kiel

[57] ABSTRACT

The invention relates to a sapphire protective covering for the distal end of endoscopes, which distal end is outfitted with an optical system and glass fibers serving to illuminate the viewing field. The sapphire protective covering substantially contains an optical tube holding the optical lens mounting, an inner tube receiving the optical tube and an outer tube enclosing the optical tube and inner tube as well as the glass fibers. The sapphire protective covering is constructed in two parts, a first part covering the optical system and a second part covering at least the light exit area of the glass fibers, and both parts are separated from one another optically at their contacting surfaces. The second part is constructed as a planar disk of determined thickness with a recess corresponding to the dimensioning of the first part. The first part can be constructed as a negative lens.

9 Claims, 2 Drawing Sheets

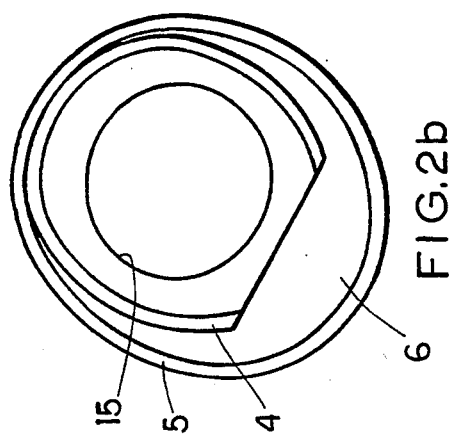
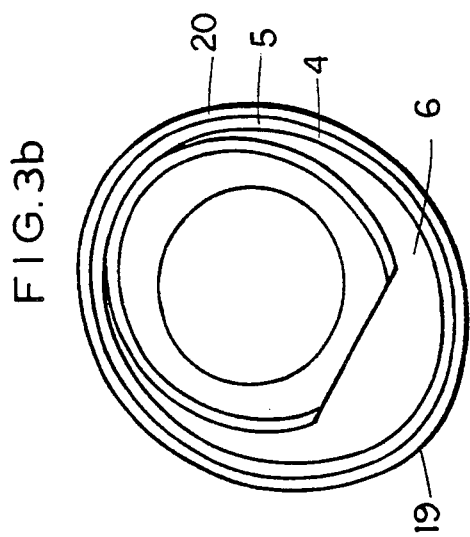
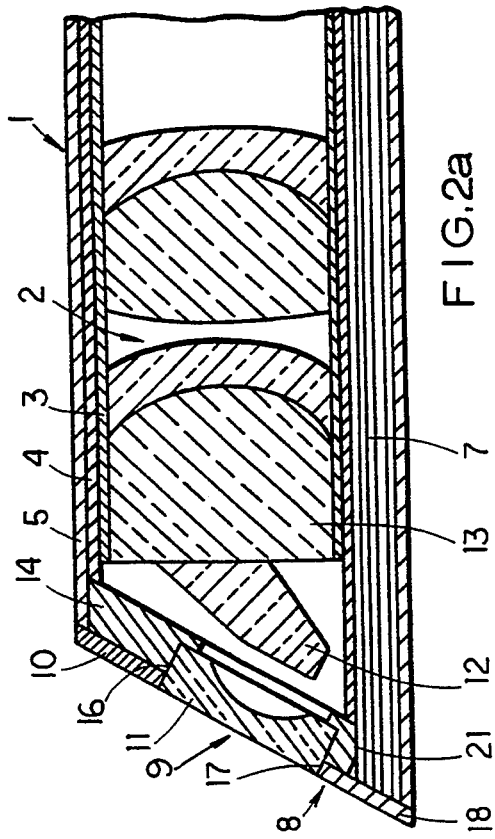
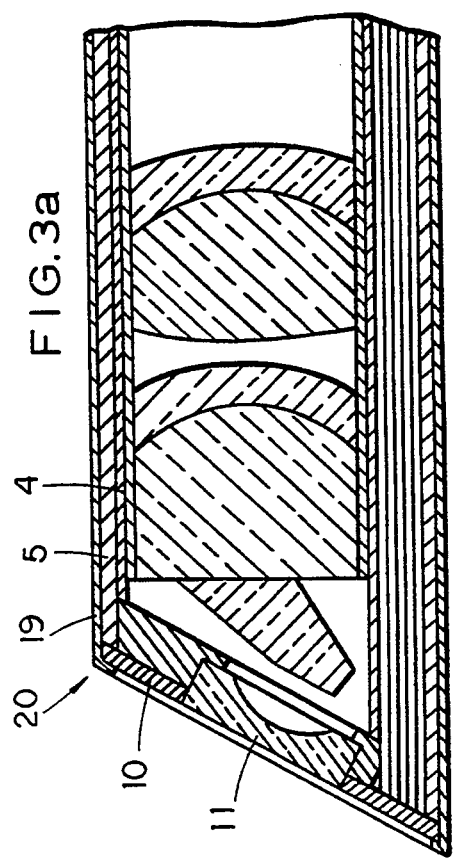

SAPPHIRE PROTECTIVE COVERING FOR MEDICAL ENDOSCOPE

BACKGROUND OF THE INVENTION

1. Field of the Invention

The invention relates to a sapphire protective covering for the distal end of endoscopes, which distal end is outfitted with an optical system and glass fibers serving to illuminate the viewing field. The sapphire protective covering substantially contains an optical tube holding the optical lens fittings or mountings, an inner tube receiving the optical tube, and an outer tube enclosing the optical tube, inner tube and glass fibers.

2. Description of the Related Art

Depending on the optical requirements imposed on an endoscope, e.g. with respect to the degree of the viewing angle, straight or angled view, etc., the distal end can be constructed so as to be beveled or at a right angle to the longitudinal axis of the endoscope.

Such endoscopes are used in areas of medicine such as arthroscopy in which it comes about time and again that the operating doctor, when removing cartilage and/or bone fragments, cuts into the tip of the endoscope with the inserted rotating instruments and damages the optical system and also the ends of the glass fibers located in this area. As a result of damage to the optical system, the operating doctor immediately loses the image of the operating field in part or in its entirety and may have to interrupt the operation.

To prevent damage to the outlet surface or exit area of the optical system it is known to provide substantially more resistant, i.e. harder, protective coverings manufactured particularly from sapphire.

The disadvantage in such protective coverings consists in that they either only protect the optical lens system or, to the extent that they simultaneously cover the ends of the glass fibers as well, cause light to be reflected into the optical system from the ends of the glass fibers which handicaps the user in such a way that he cannot clearly perceive the objects to be viewed through the optical system.

SUMMARY OF THE INVENTION

Therefore, the object of the present invention is to construct the sapphire protective covering mentioned above in such a way that the above-described disadvantages are eliminated, and further so that the ends of glass fibers which heretofore exited freely from the known endoscopes at the distal end are also covered by the protective covering and better protected during sterilization and disinfection of the endoscope.

This object is met in a sapphire protective covering for the distal end of endoscopes, which distal end is outfitted with an optical system and glass fibers serving to illuminate the viewing field, which sapphire protective covering substantially contains an optical tube holding the optical lens mountings, an inner tube receiving the optical tube, and an outer tube enclosing the optical tube, inner tube, and the glass fibers in that the sapphire protective covering is constructed in two parts, a first part covering the optical system and a second part covering at least the light exit area of the glass fibers, and both parts are divided from one another optically at their contacting surfaces.

This two-part construction of the sapphire protective covering ensures that no light reflections can penetrate from the area of the sapphire protective covering which covers the ends of the glass fibers into the optical region of same.

According to the invention, the first part of the sapphire protective covering is constructed as a circular, plane disk and the second part of the sapphire protective covering is constructed as a plane disk of determined thickness with a recess corresponding to the dimensioning of the first part. It is accordingly possible for the first part to fit exactly into the second part of the sapphire protective covering and also to center it and these two parts jointly form a smooth, plane outer surface.

In another advantageous construction of the invention, the first part is held in a holder which covers the distal end of the inner tube. This holder which is produced e.g. from metal ensures an exact and secure fit of the first part.

The second part of the sapphire protective covering advantageously lies on the holder, projects over the edge of the latter, and in particular covers the ends of the glass fibers in the vicinity of this edge. This ensures that the second part of the sapphire protective covering receives a reinforcing support and simultaneously protectively covers the ends of the glass fibers in the space between the outer tube and the inner tube.

The second part of the sapphire protective covering advantageously covers the distal end of the outer tube with its outer edge which corresponds to the outer dimensions of the distal end of the outer tube. Accordingly, the front surface of the two-part protective covering is extended to the greatest possible degree.

In a further inventive development of the sapphire protective covering, the outer tube is enclosed by a protective tube having an inner diameter which corresponds to the outer diameter of the outer tube, the distal end of the protective tube having a flanged rim which protectively surrounds the outer edge of the second part of the sapphire protective covering.

This special construction of an additional protective tube lends additional support to the sapphire protective covering and the flanged rim of the protective tube which projects slightly relative to the outer surface of the sapphire protective covering offers additional protection for the sapphire protective covering.

The first part is advantageously blackened or metallized or has a metal enclosure, at least at its edges which contact the edges of the recess in the second part of the sapphire protective covering. These steps ensure that no light reflections from the glass fibers can be reflected into the optical system between the contacting surfaces of the first part and second part of the sapphire protective covering.

In an advantageous further development of the invention, the first part is constructed as a negative lens. This construction has the advantage that no separate sapphire protective covering is needed for the negative lenses which are required in endoscopes with large viewing angles and produced from optical glass.

Finally, the inner tube can be arranged eccentrically in the outer tube and the space remaining open between the inner tube and the outer tube can be filled with glass fibers. This arrangement of the inner tube in the endoscope allows a large amount of space for the arrangement of the glass fibers in the endoscope, resulting in a relatively large light exiting surface.

BRIEF DESCRIPTION OF THE DRAWINGS

An embodiment of the invention is shown in the drawings and is described in the following:

FIG. 2a shows a section through the distal end without a protective tube;

FIG. 2b shows a top view of the two-part sapphire protective covering;

FIG. 3a shows a section according to FIG. 2a with a protective tube;

FIG. 3b shows a top view according to FIG. 2b with a protective tube.

DESCRIPTION OF THE PREFERRED EMBODIMENT

Figure 1:
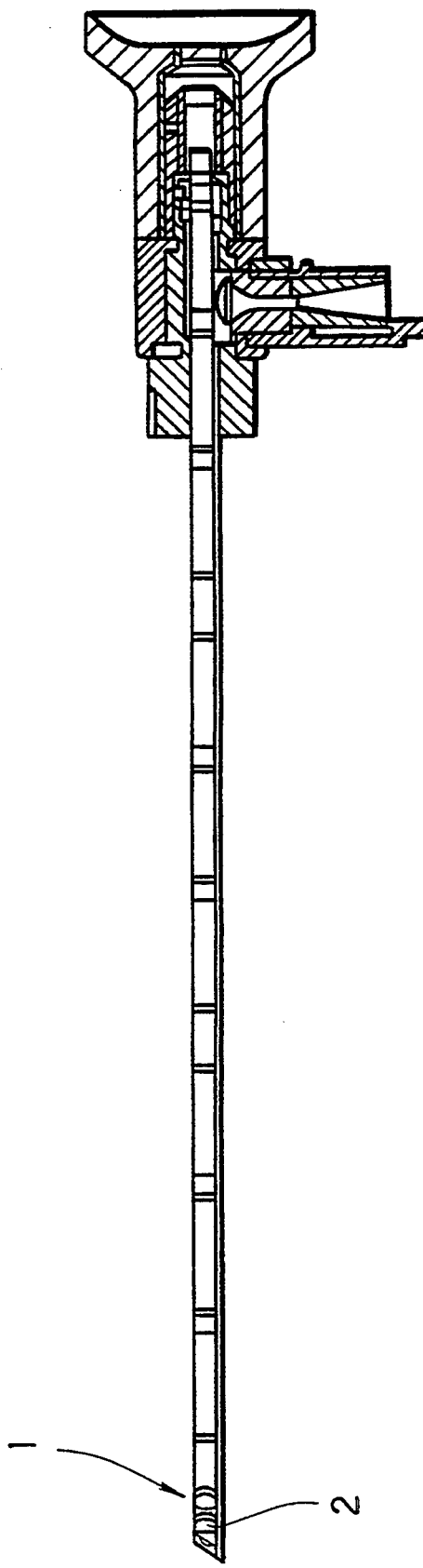
FIG. 1 shows a section through an endoscope with a distal end which is beveled at 30° relative to the longitudinal axis.

FIG. 1 shows the section through a complete medical endoscope with beveled end. Only the distal end 1 shown in FIGS. 2a to 3b is pertinent for the following.

This distal end 1 substantially includes an optical tube 3 which holds the optical lens mountings 2 and is arranged in turn in an inner tube 4.

The distal end 1 of the endoscope described in this embodiment example is constructed so as to be inclined by 30° relative to the diametral plane. The distal end of the inner tube 4 is also beveled in a corresponding manner.

Such a bevel is desirable for special considerations relating to the use of this medical endoscope 1. This bevel can also be constructed with a different angle.

The inner tube 4 is enclosed in turn by an outer tube 5 which likewise has a distal end which is beveled by 30°, the inner tube 4 being arranged eccentrically in this outer tube 5 so that a space 6 remains open between the two tubes. This space 6 is filled with glass fibers 7 serving to guide light. The beveled distal end of the outer tube 5 is completely covered by the sapphire protective covering 8. This sapphire protective covering 8 is constructed in two parts, namely a first part 9 covering the optical system and a second part 10 covering the remaining area, particularly the light exit area of the glass fibers 7.

The first part 9 of the sapphire protective covering 8 could be constructed as a simple, plane disk having a determined thickness and without effecting the travel of light. However, the endoscope described in this embodiment example has a viewing angle of approximately 100° and requires a negative lens, for which reason the sapphire protective covering 8 is constructed as such a negative lens 11.

In view of the inclined arrangement of the negative lens 11 due to the beveling of the distal end 1 of the endoscope, it is necessary to arrange a prism 12 at the front lens 13 of the lens mountings 2.

The negative lens 11 is held in a holder 14 having a straightedge 21, holder 14 is adapted to the beveled end of the inner tube 4 and is soldered to the latter, for example.

The second part 10 of the sapphire protective covering 8 has a recess 15 corresponding to the radial dimensions of the negative lens 11. The negative lens 11 projects into this recess 15 and simultaneously centers the second part 10 of the sapphire protective covering 8.

At least the contacting edges 16 and 17 of the negative lens 11 and those of the recess 15 in the second part 10 of the sapphire protective covering 8 are provided with opaque means, i.e. edges 16 and 17 are blackened or metallized so that light reflections from the area of the second part 10 of the sapphire protective covering 8 covering the glass fiber ends 18 are prevented in every case from being reflected into the negative lens 11 and accordingly into the optical system of the endoscope.

This two-part construction of the protective covering 8 of the distal end 1 of the endoscope, which protective covering 8 is produced from sapphire, prevents the optical system and glass fibers from being destroyed by the rotating medical tools in the operating field.

This sapphire protective covering 8 further protects the glass fiber ends 18 during sterilization and disinfection, particularly when sterilizing with steam. In the absence of such protection, disinfectants and hot-water steam attack or corrode the polished surface of the glass fiber ends 18 and accordingly considerably impair the transmission of light. In conventional endoscopes it was always necessary to repolish the glass fiber exit areas.

To further protect the above-described distal end 1 of an endoscope, the outer tube 5 is enclosed by a protective tube 19 having an inner diameter corresponding to the outer diameter of the outer tube 5, the distal end of the protective tube 19 having a flanged rim 20 which protectively encloses the outer edge of the second part 10 of the sapphire protective covering 8.

What is claimed is:

1. A protective covering for a distal end of an endoscope, the distal end being outfitted with an optical system and glass fibers serving to illuminate a viewing field, the endoscope including an optical tube for holding optical lens mountings, an inner tube for receiving the optical tube, and an outer tube for enclosing the optical tube, inner tube, and the glass fibers, the protective covering comprising:

a first part and a second part, the first and second parts being constructed from sapphire, the first part for performing an optical function and being held in a holder which covers a distal end of the inner tube, the holder having an opening defining an optical path of observation, and the second part covering the remaining end surface of the distal end of the endoscope, and the two parts being separated at a common contacting surface by opaque means for preventing the reflection of light from the glass fibers into the optical system, the protective covering entirely covering the distal end of the endoscope, the glass fibers being guided directly up to the protective covering.

2. The protective covering according to claim 1 wherein the first part is constructed as a circular, planar disk of determined thickness.

3. The protective covering according to claim 1 wherein the second part is constructed as a planar disk of determined thickness with a recess for receiving the first part.

4. The protective covering according to claim 3 wherein the second part rests on the holder, the second part projecting over an edge of the holder and covering glass fibers adjacent to the edge.

5. The protective covering according to claim 4 wherein the second part covers a distal end of the outer tube with an outer edge.

6. The protective covering according to claim 1 wherein the outer tube is enclosed by a protective tube having an inner diameter which corresponds to an outer diameter of the outer tube, a distal end of the protective tube having a flanged rim which protectively surrounds an outer edge of the second part.

7. The protective covering according to claim 1 wherein said opaque means include a blackened or metallized edge or a metal enclosure at an edge of said first part which contacts an edge of the recess in the second part.

8. The protective covering according to claim 1 wherein the first part is constructed as a negative lens.

9. The protective covering according to claim 1, wherein the inner tube is arranged eccentrically in the outer tube and the glass fibers are predominantly arranged in a space between the inner tube and the outer tube, the glass fibers completely filling the space.

* * * * *